United States Patent
Kang et al.

(10) Patent No.: US 11,774,433 B2
(45) Date of Patent: Oct. 3, 2023

(54) METHOD FOR CHARACTERIZING GRAPHENE ON PLATINUM SUBSTRATE

(71) Applicant: SHANGHAI INSTITUTE OF MICROSYSTEM AND INFORMATION TECHNOLOGY, CHINESE ACADEMY OF SCIENCES, Shanghai (CN)

(72) Inventors: He Kang, Shanghai (CN); Guanghui Yu, Shanghai (CN); Yanhui Zhang, Shanghai (CN); Zhiying Chen, Shanghai (CN)

(73) Assignee: SHANGHAI INSTITUTE OF MICROSYSTEM AND INFORMATION TECHNOLOGY, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 17/952,304

(22) Filed: Sep. 25, 2022

(65) Prior Publication Data

US 2023/0160868 A1 May 25, 2023

(30) Foreign Application Priority Data

Nov. 24, 2021 (CN) .......................... 202111404530.9

(51) Int. Cl.
G01N 33/208 (2019.01)
G01N 21/78 (2006.01)

(52) U.S. Cl.
CPC .......... *G01N 33/208* (2019.01); *G01N 21/78* (2013.01)

(58) Field of Classification Search
None
See application file for complete search history.

(56) References Cited

U.S. PATENT DOCUMENTS

2019/0094147 A1   3/2019   Heineman et al.

FOREIGN PATENT DOCUMENTS

CN   102749291 A   10/2012
CN   103353437 A   10/2013
(Continued)

OTHER PUBLICATIONS

Mehmet Harbi Calimli, et al., Preparation, characterization and adsorption kinetics of methylene blue dye in reduced-graphene oxide supported nanoadsorbents, «Journal of Molecular Liquids», Jul. 1, 2020, vol. 309. p. 1-10, Elsevier, Netherlands.

(Continued)

*Primary Examiner* — Xiaoyun R Xu

(57) ABSTRACT

A method for characterizing graphene on a platinum substrate, including: coating a methylene blue developing solution to a platinum substrate having a surface covered with graphene, so that the methylene blue developing solution reacts with hydrogen-containing gas under catalysis of platinum to yield colorless methylene white; after the pressure is restored, methylene white in the exposed area of platinum substrate will quickly turn blue when it is oxidized into methylene blue by reacting with oxygen in the air under catalysis of platinum. Thus, color difference can be formed to facilitate the observation of the graphene. The characterization method is highly reproducible and simple, and can be used to characterize graphene with a large area on a platinum substrate. The characterization method does not damage the graphene and platinum substrate, has no negative impact on the quality of graphene, and the platinum substrate can be recycled to reduce costs.

9 Claims, 3 Drawing Sheets

(56) References Cited

FOREIGN PATENT DOCUMENTS

| | | |
|---|---|---|
| CN | 104568554 A | 4/2015 |
| CN | 105021621 A | 11/2015 |
| JP | 2018179836 A | 11/2018 |

OTHER PUBLICATIONS

Zheng, Haifu et al., The Preparation and Characterization of Graphene by Alkali Reduction Method, »J. Changchun Inst. Tech.(Nat. Sci. Edi.)», Jun. 15, 2019, vol. 20, No. 2. p. 108-111. JSIM, China.

METHOD FOR CHARACTERIZING GRAPHENE ON PLATINUM SUBSTRATE

CROSS REFERENCE TO RELATED APPLICATION

This application claims the benefits of priority to Chinese Patent Application No. CN 202111404530.9, entitled "METHOD FOR CHARACTERIZING GRAPHENE ON PLATINUM SUBSTRATE", filed with CNIPA on Nov. 24, 2021, the contents of which are incorporated herein by reference in its entirety.

BACKGROUND

Field of Disclosure

The present disclosure relates to the technical field of two-dimensional material characterization, and in particular, to a method for characterizing graphene on a platinum substrate.

Description of Related Arts

In recent years, graphene has attracted a lot of research attention due to its unique properties and wide applications. The preparation of high-quality materials is the basis for theoretical research and application, and accurate and convenient access to obtain information of material quality is essential for both material growth research and device manufacturing.

Currently, there are many techniques suitable for characterization of graphene quality, such as STM, TEM, and AFM, which can be used to characterize fine structures of graphene such as atomic arrangement and various defects. However, these characterization techniques are expensive, difficult to use, and destructive to the sample, and much smaller observation area due to high magnification, which is not conducive to large-scale characterization of the sample quality.

Due to the low solubility of carbon in copper and the low price of copper, copper-based substrates have been widely used for mono-layer graphene preparation. Due to the difference in oxidation resistance between copper and graphene, when a graphene-on-copper sample is slightly oxidized, its graphene-covered surfaces and exposed surfaces will be significantly different in color due to oxidation. Then the crystalline domains of the graphene on a scale from micron to millimeter can be clearly observed by an optical microscope, which enables a quick assessment of shapes, sizes, and distribution of the crystalline domains within a large area.

Compared with copper substrates, the growth of graphene on platinum substrate has the advantages of fast speed, good oxidation resistance and so on, and therefore has been garnering more and more attention. But since platinum is oxidation-resistant, graphene on platinum substrates cannot be observed by optical microscopes using the oxidation method. The distribution of crystalline domains of graphene on platinum surfaces can only be observed by SEM, which requires a long test process and is not suitable for wafer-level sample characterization.

Therefore, it is necessary to provide a method for the characterization of graphene on platinum substrates.

SUMMARY

The present disclosure provides a method for characterizing graphene on a platinum substrate, which includes the following steps:

preparing methylene blue (MB) developing solution;

coating a platinum substrate with the methylene blue developing solution to obtain a sample, wherein the platinum substrate has a surface covered with graphene;

placing the sample in a reactor, and introducing hydrogen-containing gas;

when a color change occurs in the sample, performing a vacuuming process to evaporate the solvent of the methylene blue developing solution;

unloading the vacuum, and observing the sample in the air;

and after the observation, removing residue of the methylene blue developing solution.

Optionally, the solvent of the methylene blue developing solution includes one or a combination of aqueous solution, alcohol solution, and acetone solution; the concentration of methylene blue in the methylene blue developing solution is in a range of 0.2 g/L-2.0 g/L.

Optionally, the platinum substrate includes one of a platinum film, a platinum alloy film, a platinum foil, and a platinum bulk; the platinum alloy includes one or a combination of copper platinum, iron platinum, cobalt platinum, nickel platinum, chromium platinum, tungsten platinum, molybdenum platinum, and manganese platinum.

Optionally, a method of coating the platinum substrate with the graphene includes preparing the graphene on the surface of the platinum substrate using a chemical vapor deposition method, or transferring prepared graphene to the surface of the platinum substrate.

Optionally, the covering of the graphene on the surface of the platinum substrate includes complete covering or partial covering, where the partial covering includes partial covering according to a predetermined pattern.

Optionally, the method of coating the platinum substrate with the methylene blue developing solution includes one or a combination of spraying, spin-coating, and drop-casting.

Optionally, the hydrogen-containing gas includes one or a combination of pure hydrogen, hydrogen-nitrogen gas mixture, and hydrogen-argon gas mixture. The hydrogen-containing gas has a hydrogen concentration in a range of 5%-100%, and a pressure in a range of 1 kPa to 1000 kPa.

Optionally, the temperature within the reactor is in a range of 5° C. to 90° C. when the hydrogen-containing gas is introduced for reaction.

Optionally, the pressure inside the reactor during the vacuuming process is in a range of 0.001 kPa-70 kPa.

Optionally, a device for observing the sample includes an optical microscope or an electrical microscope;

the method of removing the residue of the methylene blue developing solution includes rinsing using one or a combination of aqueous solution, alcohol solution, or acetone solution.

As described above, the present disclosure provides a method for characterizing graphene on a platinum substrate, including: coating the platinum substrate with a methylene blue developing solution, with the platinum substrate having a surface covered with graphene, so that the methylene blue developing solution reacts with hydrogen-containing gas under the catalysis of platinum to yield colorless methylene white; performing a vacuuming process to evaporate the methylene blue developing solution; after the pressure is restored, the methylene white in the exposed area of the platinum substrate can be oxidized into methylene blue by reacting with oxygen in the air under the catalysis of platinum, at which time the exposed platinum area quickly turns blue. Thus, the color difference can be formed to facilitate the observation of the graphene. The reactions of the present disclosure can be performed spontaneously without heating. The characterization method is highly reproducible and simple, and can be used to characterize graphene with a large area on a platinum substrate. In addition, the characterization method does not damage the graphene and the platinum substrate, has no negative impact on the quality of graphene, and the platinum substrate can be recycled to reduce costs.

DETAILED DESCRIPTION

The embodiments of the present disclosure will be described below. Those skilled in the art can easily understand other advantages and effects of the present disclosure according to contents disclosed by the specification. The present disclosure may also be implemented or applied through other different specific implementation modes. Various modifications or changes may be made to all details in the specification based on different points of view and applications without departing from the spirit of the present disclosure.

As in the detailed description of the embodiments of the present disclosure, for the purpose of illustration, the cross-sectional drawings representing the structure of the device will not be locally enlarged according to the general scale, and the schematic drawings are only examples, which should not limit the protection scope of the present disclosure herein. In addition, the actual production should include the length, width and depth of the three-dimensional size.

The terms regarding spatial relationships such as "under," "below," "lower," "underneath," and "on," "above," etc., are used for convenience of description to describe the relationship of one element or feature to another element or feature in a figure. It should be understood that in addition to the orientation shown in the figure, the spatial relationship terms are intended to include different orientations during use and operation. In addition, when a layer is referred to as being "between" two layers, it may be the only layer between the two layers, or one of a plurality of layers between the two layers. As used herein, "between . . . " means including both endpoint values.

In the context of the present disclosure, the structure described with a first feature "on top" of a second feature may include embodiments where the first and second features are formed in direct contact, or may include embodiments where additional features are formed between the first and second features such that the first and second features may not be in direct contact.

It needs to be stated that the drawings provided in the following embodiments are just used for schematically describing the basic concept of the present disclosure, thus only illustrating components only related to the present disclosure and are not drawn according to the numbers, shapes and sizes of components during actual implementation, the configuration, number and scale of each component during actual implementation thereof may be freely changed, and the component layout configuration thereof may be more complicated.

Figure 1:
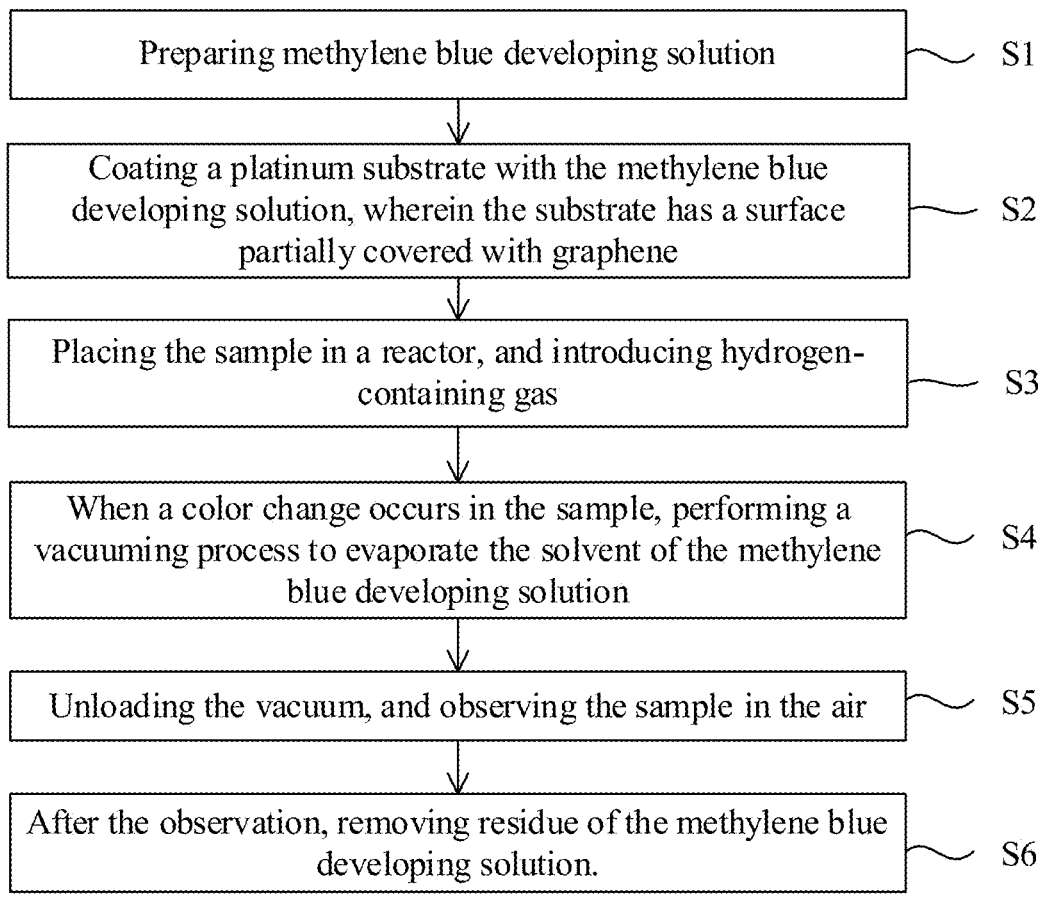
FIG. 1 shows a schematic flowchart of the method for characterizing graphene on a platinum substrate according to an embodiment of the present disclosure.

As shown in FIG. 1, the present disclosure provides a method for characterizing graphene on a platinum substrate, which specifically includes the following steps:

Step S1: preparing methylene blue developing solution.

As an example, the solvent of the methylene blue developing solution used in the method includes one or a combination of aqueous solution, alcohol solution, and acetone solution; the concentration of methylene blue in the methylene blue developing solution is in a range of 0.2 g/L-2.0 g/L.

Specifically, methylene blue (MB) is an organic stain, and is highly soluble in water and alcohol, etc. A methylene blue solution is blue in color. Methylene blue can react with hydrogen under the catalysis of platinum to yield colorless methylene white, and methylene white can be oxidized into methylene blue by reacting with oxygen under the catalysis of platinum, so as to quickly change to blue. Thus, color differences can be formed by using methylene blue, which facilitates the characterization of graphene. The above reactions are very rapid and can be performed spontaneously without the need of heating.

Further, graphene can adsorb methylene blue, and thus methylene blue can be used for convenient and effective characterization of graphene on platinum substrates.

The solvent of the methylene blue developing solution may be one or a combination of aqueous solution, alcohol solution, and acetone solution. However, the solvent is not limited thereto, and other solvents may be used for preparing the methylene blue developing solution. The concentration of methylene blue in the methylene blue developing solution may be in a range of 0.2 g/L-2.0 g/L, such as 0.2 g/L, 0.5 g/L, 1 g/L, 1.5 g/L, 2.0 g/L.

Then step S2: coating a platinum substrate having a surface covered with graphene with the methylene blue developing solution.

As an example, the platinum substrate may include one of a platinum film, a platinum alloy film, a platinum foil, and a platinum bulk; the platinum alloy may include one or a combination of copper platinum, iron platinum, cobalt platinum, nickel platinum, chromium platinum, tungsten platinum, molybdenum platinum, and manganese platinum.

As an example, a method of covering the platinum substrate with the graphene may include preparing the graphene on the surface of the platinum substrate using a chemical vapor deposition method, or transferring the previously-prepared graphene to the surface of the platinum substrate.

As an example, the covering of the graphene on the surface of the platinum substrate includes complete covering or partial covering, where the partial covering includes partial covering according to a predetermined pattern.

As an example, the method of coating with platinum substrate with the methylene blue developing solution may include one or a combination of spraying, spin-coating, and drop-casting.

Specifically, the platinum substrate may include one of a platinum film, a platinum alloy film, a platinum foil, and a platinum bulk; the platinum alloy may include one or a combination of copper platinum, iron platinum, cobalt platinum, nickel platinum, chromium platinum, tungsten platinum, molybdenum platinum, and manganese platinum. That is, the substrate includes at least platinum in order to facilitate subsequent reactions.

Specifically, a method of covering the platinum substrate with the graphene may include preparing the graphene on the surface of the platinum substrate using a chemical vapor deposition (CVD) method, or transferring previously-prepared graphene to the surface of the platinum substrate by means of a transferring method.

Further, the covering of the graphene on the surface of the platinum substrate may include complete covering or partial covering, where the partial covering may include partial covering according to a predetermined pattern. In the present disclosure, there is no limitation as to the morphology of the graphene, thereby allowing for an expanded scope of application.

Methods of coating with the methylene blue developing solution include the following: in one embodiment, the methylene blue developing solution may be applied dropwise using a dropper to the platinum substrate partially covered with graphene; in another embodiment, the methylene blue developing solution may be sprayed using a sprayer to the platinum substrate having a surface covered with graphene (that is, partially covered with graphene). Of course, the methylene blue developing solution may be applied dropwise to the platinum substrate partially covered with graphene using a spin-coating method or a method combining spraying, spin-coating, and drop-casting.

Then step S3: placing the sample obtained in step S2 in a reactor, and introducing hydrogen-containing gas.

As an example, the hydrogen-containing gas may include one or a combination of pure hydrogen, hydrogen-nitrogen gas mixture and hydrogen-argon gas mixture. The hydrogen-containing gas has a hydrogen concentration in a range of 5%-100%, and a pressure in a range of 1 kPa to 1000 kPa.

As an example, during the reaction between the methylene blue and hydrogen in the reactor, the temperature within the reactor is in a range of 5° C. to 90° C.

Specifically, the hydrogen-containing gas can react with methylene blue under the catalysis of platinum to yield colorless methylene white; after vacuum unloading in the subsequent process, methylene white in the exposed area of the platinum substrate can be oxidized into methylene blue by reacting with oxygen in the air under the catalysis of platinum, making the exposed platinum area blue firstly. Thus, the color difference can be formed to facilitate the observation of the graphene. The hydrogen-containing gas may include one or combination of pure hydrogen, hydrogen-nitrogen gas mixture, and hydrogen-argon gas mixture. Preferably, the hydrogen-containing gas has a hydrogen concentration in a range of 5%-100%, such as 5%, 10%, 20%, 50%, 80%, 100% and other values in the range, and a pressure in a range of 1 kPa to 1000 kPa, such as 1 kPa, 10 kPa, 100 kPa, 500 kPa, 1000 kPa and other values in the range, to speed up the reaction.

Further, during the reaction between the methylene blue and the hydrogen, preferably, the temperature within the reactor is in a range of 5° C. to 90° C., such as 5° C., 10° C., 25° C., 50° C., 80° C., 90° C., and any other values in the range, to further accelerate the reaction. However, the temperature within the reactor during the reaction is not limited thereto, the reaction can also be carried out spontaneously without heating, depending on the need for adaptation of the reaction conditions.

Next, step S4: when the sample undergoes a color change from blue to colorless, performing a vacuuming process to evaporate the methylene blue developing solution.

As an example, the pressure during the vacuuming process is in a range of 0.001 kPa-70 kPa.

Specifically, in one example, as soon as the color change of the sample has occurred, the vacuuming process is performed to evaporate the solvent of the methylene blue developing solution. The pressure during the vacuuming process may be in a range of 0.001 kPa-70 kPa, such as 0.001 kPa, 0.1 kPa, 1 kPa, 10 kPa, 50 kPa, 70 kPa, and any other value in the range, which may be specifically adapted to actual needs.

Then step S5: unloading the vacuum, and observing the sample. Herein, unloading the vacuum refers to restoring the reactor to that of the atmosphere so that the sample can be taken out of the reactor safely.

After unloading the vacuum, the device for observing the sample may include an optical microscope, or an electrical microscope such as a scanning electron microscope (SEM). The selection of the device for observing the sample is not overly limited herein.

Then step S6: after the observation, removing the residue of the methylene blue developing solution.

As an example, the method of removing the residue of the methylene blue developing solution may include rinsing using one or a combination of aqueous solution, alcohol solution, or acetone solution. The residue of the methylene blue developing solution may be in a form of liquid or solid. Preferably, the residue of the methylene blue developing solution is in a form of solid upon the evaporation of the solvent of the methylene blue developing solution in step S4 and the unloading of vacuum in step S5.

Specifically, the method of removing the residue of the methylene blue developing solution may include rinsing the sample in a liquid that can dissolve methylene blue, such as rinsing the sample in deionized water, acetone solution or alcohol. The method of removing the residue of the methylene blue developing solution is not overly limited herein.

Based on the chemical reaction between methylene blue and hydrogen under the catalysis of platinum, the characterization of graphene on the platinum surface can be realized. The blue methylene blue in the developing solution can be reduced to colorless methylene white by hydrogen under the catalysis of platinum. At this time, the methylene blue can move freely in the solution. All the methylene blue on the graphene and on exposed areas of the platinum substrate is reduced to methylene white, which will then remain where it was after the evaporation of the solvent. The "exposed areas of the platinum substrate" herein refers to the portion of the platinum substrate that is not covered by graphene. After unloading the vacuum, methylene white in the exposed areas of the platinum substrate can be oxidized into methylene blue by reacting with oxygen in the air under the catalysis of platinum, making the exposed platinum areas turn blue. The method for characterizing graphene according to the present disclosure is highly reproducible and simple, and can be used to characterize graphene with a large area, such as wafer-level graphene. In addition, the method for characterizing graphene according to the present disclosure does not damage the graphene and platinum substrate, thus the platinum substrate can be recycled, without affecting on the quality of graphene.

The following will be used to further explain and illustrate the technical solutions in the present disclosure. Specifically, the method may also include:

preparing alcoholic solution of methylene blue at a concentration of 0.6 g/L;

dropwise applying the alcoholic solution of methylene blue to a surface of a platinum film where single crystalline domains of graphene have grown;

placing the sample coated with the alcoholic solution of methylene blue into a reaction chamber, and introducing pure hydrogen gas into the reaction chamber; the temperature in the reaction chamber is 25° C. and the pressure inside the reaction chamber is 101 kPa;

after the color of the alcoholic solution changes from blue to colorless, performing vacuuming until the pressure of the reaction chamber is 30 kPa, to evaporate the ethanol in the alcoholic solution of methylene blue;

unloading the vacuum, and observing the sample; and after the observation, rinsing the sample with deionized water to remove the residue of methylene blue.

Figure 2:
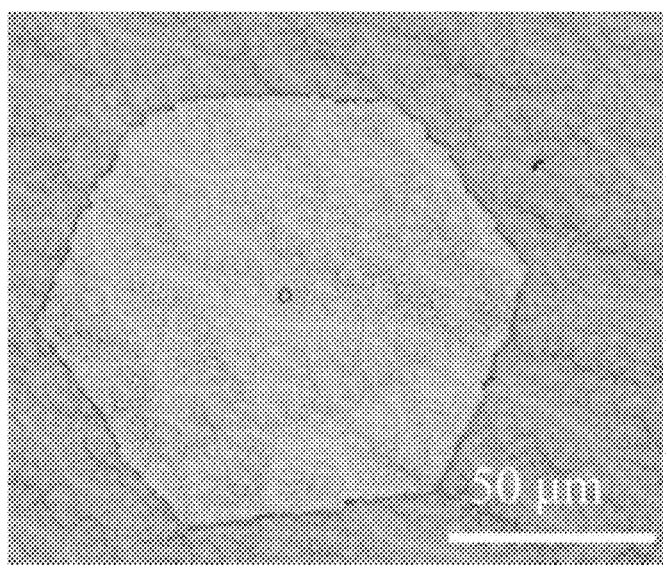
FIG. 2 shows an optical micrograph of a single crystalline domain of graphene on a platinum film after treatment of methylene blue developing solution, according to an embodiment of the present disclosure.
Figure 3:
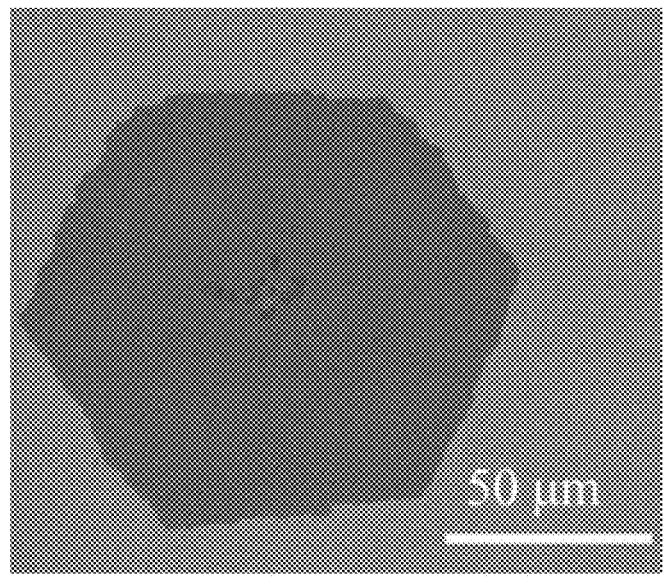
FIG. 3 shows a scanning electron microscope (SEM) image of a single crystalline domain of graphene on a platinum film after rinsing for removal of the developing solution, according to an embodiment of the present disclosure.

FIG. 2 shows an optical micrograph of a single crystalline domain of graphene on the platinum film after the methylene blue treatment; FIG. 3 shows the corresponding SEM image of the single crystalline domain of graphene on the platinum film after rinsing. As shown in FIGS. 2-3, it can be seen that after methylene blue development, the characterization by the optical micrograph is consistent with that of the SEM image.

Figure 4:
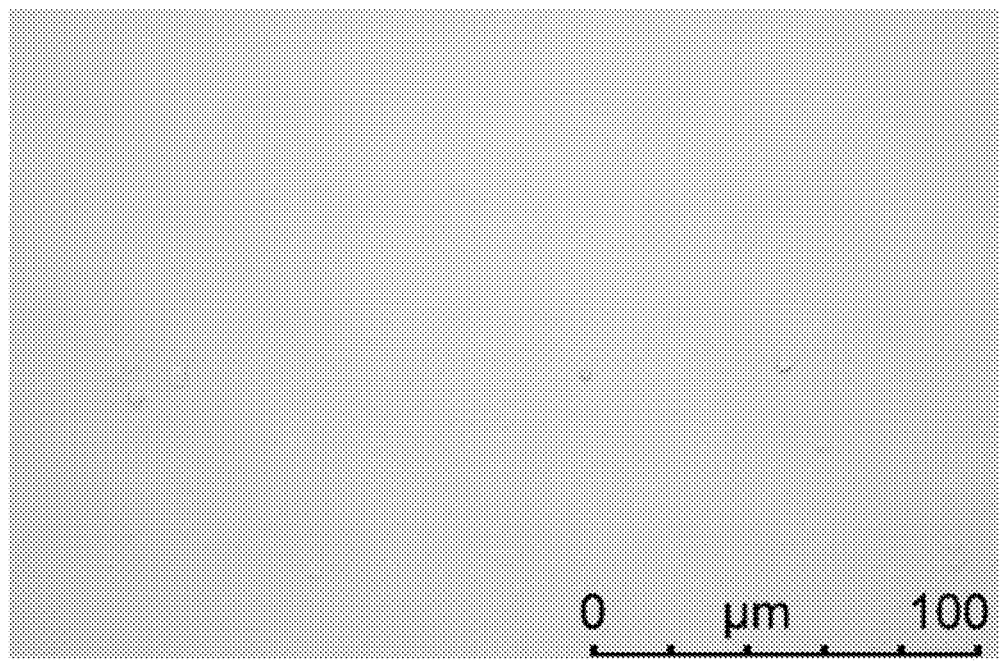
FIG. 4 shows an optical micrograph of a single crystalline domain of graphene on a platinum film after rinsing for removal of the developing solution, according to an embodiment of the present disclosure.

FIG. 4 shows an optical micrograph of single crystalline domains of graphene on the platinum film after rinsing for removal of the developing solution. As shown in FIG. 4, no methylene blue remains on the surface of the platinum film.

Figure 5:
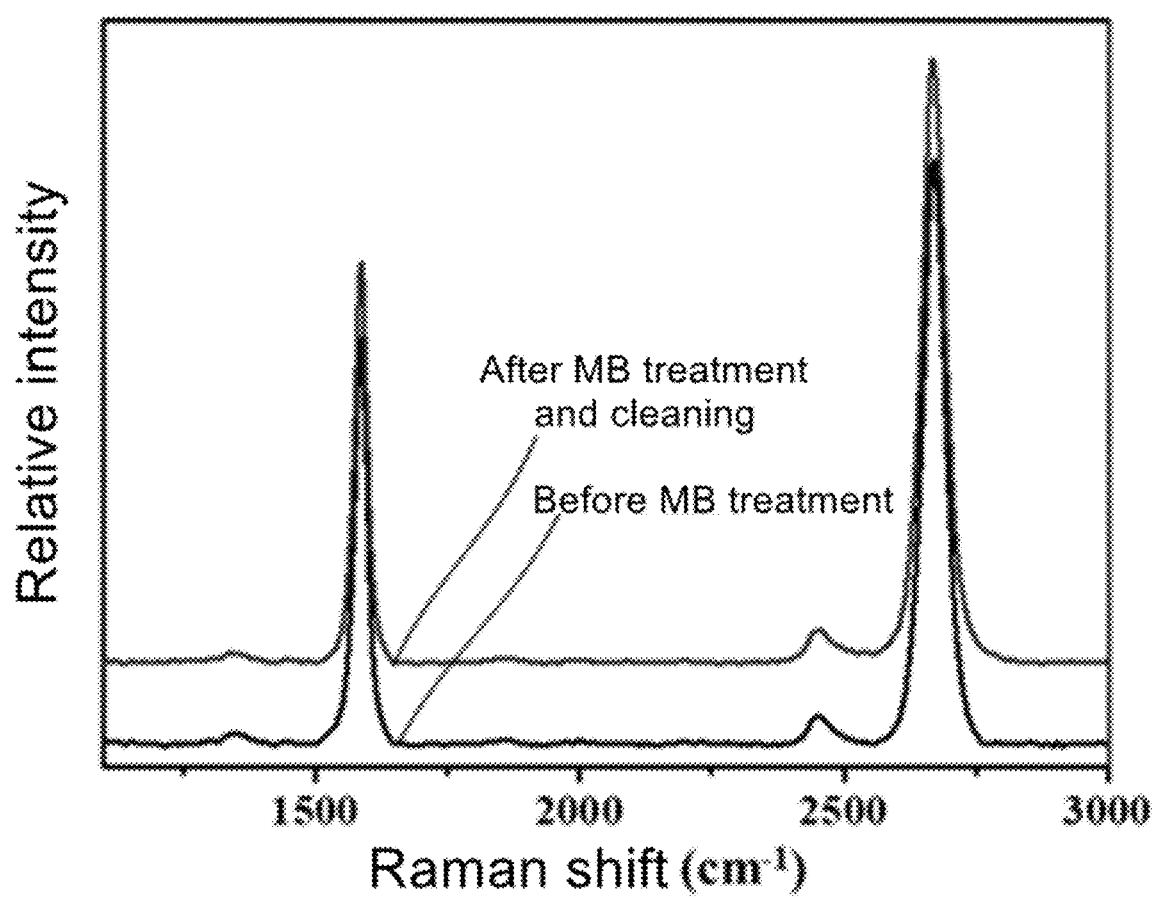
FIG. 5 shows a Raman spectra diagram of graphene transferred to a $SiO_2$ substrate before the treatment of methylene blue developing solution and after rinsing, according to an embodiment of the present disclosure.

FIG. 5 shows a Raman spectra diagram of the graphene transferred to $SiO_2$ before the methylene blue treatment and after rinsing, from which it can be clearly seen that the positions of 2D peak (2670 $cm^{-1}$) and G peak (1580 $cm^{-1}$) of the graphene have not shifted after the methylene blue treatment, indicating that the crystal quality of the graphene before and after the methylene blue treatment is the same, and the methylene blue has no destructive effect on the graphene.

In summary, the present disclosure provides a method for characterizing graphene on a platinum substrate, including: coating a platinum substrate having a surface covered with graphene with methylene blue developing solution, so that the methylene blue developing solution reacts with hydrogen-containing gas under the catalysis of platinum to yield colorless methylene white; performing a vacuuming process to evaporate the methylene blue developing solution; after the pressure is restored, methylene white in the exposed area of the platinum substrate will quickly turn blue when it is oxidized into methylene blue by reacting with oxygen in the air under the catalysis of platinum. Thus, the color difference can be formed to facilitate the observation of the graphene. The reactions of the present disclosure can be performed spontaneously without heating. The characterization method is highly reproducible and simple, and can be used to characterize graphene with a large area on a platinum substrate. In addition, the characterization method does not damage the graphene and the platinum substrate, has no negative impact on the quality of graphene, and the platinum substrate can be recycled to reduce costs.

The above-mentioned embodiments are merely illustrative of the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

What is claimed is:

1. A method for characterizing graphene on a platinum substrate, comprising the following steps:

preparing methylene blue developing solution;

coating a platinum substrate with the methylene blue developing solution to obtain a sample, wherein the platinum substrate has a surface partially covered with graphene;

placing the sample in a reactor, and introducing a hydrogen-containing gas;

when a color change occurs in the sample, performing a vacuuming process to evaporate a solvent of the methylene blue developing solution;

unloading the vacuum, and observing the sample; and after the observation, removing residue of the methylene blue developing solution, wherein a device for observing the sample comprises an optical microscope or an electrical microscope; a method of removing the residue of the methylene blue developing solution comprises rinsing using one or a combination of aqueous solution, alcohol solution, and acetone solution.

2. The method for characterizing graphene on a platinum substrate according to claim 1, wherein a solvent of the methylene blue developing solution includes one or a combination of aqueous solution, alcohol solution, and acetone solution; a concentration of methylene blue in the methylene blue developing solution is in a range of 0.2 g/L-2.0 g/L.

3. The method for characterizing graphene on a platinum substrate according to claim 1, wherein the platinum substrate includes one of a platinum film, a platinum alloy film, a platinum foil, and a platinum bulk; wherein the platinum alloy includes one or a combination of copper platinum, iron platinum, cobalt platinum, nickel platinum, chromium platinum, tungsten platinum, molybdenum platinum, and manganese platinum.

4. The method for characterizing graphene on a platinum substrate according to claim 1, wherein a method of covering the platinum substrate with the graphene comprises preparing the graphene on the surface of the platinum substrate using a chemical vapor deposition method, or transferring previously-prepared graphene to the surface of the platinum substrate.

5. The method for characterizing graphene on a platinum substrate according to claim 1, wherein the covering of the graphene on the surface of the platinum substrate comprises complete covering or partial covering, wherein the partial covering comprises partial covering according to a predetermined pattern.

6. The method for characterizing graphene on a platinum substrate according to claim 1, wherein a method of coating the platinum substrate with the methylene blue developing solution comprises one or a combination of spraying, spin-coating, and drop-casting.

7. The method for characterizing graphene on a platinum substrate according to claim 1, wherein the hydrogen-containing gas comprises one or a combination of pure hydrogen, hydrogen-nitrogen gas mixture, and hydrogen-argon gas mixture; wherein the hydrogen-containing gas has a hydrogen concentration in a range of 5%-100%, and a pressure in a range of 1 kPa to 1000 kPa.

8. The method for characterizing graphene on a platinum substrate according to claim 1, wherein a temperature within the reactor is in a range of 5° C. to 90° C. when the hydrogen-containing gas is introduced for reaction.

9. The method for characterizing graphene on a platinum substrate according to claim 1, wherein a pressure inside the reactor during the vacuuming process is in a range of 0.001 kPa-70 kPa.

* * * * *